United States Patent [19]

Shimizu et al.

[11] Patent Number: 4,565,801
[45] Date of Patent: Jan. 21, 1986

[54] HETEROPOLY-ACIDS AND THEIR PRODUCTION AND USE

[75] Inventors: Shinkichi Shimizu; Hiroshi Ichihashi; Koichi Nagai, all of Niihama, Japan

[73] Assignee: Sumitomo Chemical Company, Limited, Osaka, Japan

[21] Appl. No.: 371,223

[22] Filed: Apr. 23, 1982

[30] Foreign Application Priority Data

Apr. 24, 1981 [JP] Japan .................. 56-62710

[51] Int. Cl.[4] ............................................. B01J 27/14
[52] U.S. Cl. ................... 502/209; 423/306; 423/307; 502/211; 562/535
[58] Field of Search ................. 423/308, 306, 307; 562/535; 502/209, 211

[56] References Cited

U.S. PATENT DOCUMENTS

| | | | |
|---|---|---|---|
| 2,881,212 | 4/1959 | Idol et al. | 502/211 |
| 2,900,235 | 8/1959 | Arnold et al. | 502/211 |
| 3,379,652 | 4/1968 | Young | 502/211 |
| 3,654,354 | 4/1972 | Blanc | 502/209 |
| 4,146,574 | 3/1979 | Onoda et al. | 502/211 |
| 4,180,678 | 12/1979 | Wada et al. | |
| 4,192,951 | 3/1980 | Slinkard et al. | 502/209 |
| 4,321,160 | 3/1982 | Farrington et al. | 502/209 |

FOREIGN PATENT DOCUMENTS

| | | | |
|---|---|---|---|
| 0013578 | 1980 | European Pat. Off. | 502/209 |
| 1372476 | 8/1964 | France | 502/209 |
| 23013 | 8/1975 | Japan | |
| 90214 | 8/1978 | Japan | 502/209 |
| 14089 | 6/1979 | Japan | |
| 822140 | 2/1958 | United Kingdom | |

OTHER PUBLICATIONS

George A. Tsigdinos and C. J. Hallada, "Molybdovanadophosphoric Acids and Their Salts, I. Investigation of Methods of Preparation and Characterization", *Inorganic Chemistry*, vol. 7, No. 3 (Mar. 1968), pp. 437-441.

H. T. Evans, Jr., "Perspect. Struct. Chem.", 4, 1 (1971), pp. 1-21, 56-59.

Ind. & Chem. Eng. Prod. Res. and Development, vol. 13, No. 4, pp. 267-274 (1974).

J. Phy. Chem., vol. 71, pp. 1265-1270 (1967).

C. J. Clark et al., Acta Cryst., B32, 1545 (1976), pp. 1545-1547.

H. D'Amour et al., Z. Kristallogr., 143, 1 (1976), pp. 1-13.

A. Suteu et al., Rev. Roum. Chem., 15, 1653 (1970), pp. 1563-1572.

J. W. Illingworth et al., J. Chem. Soc., 1935, 575.

*Primary Examiner*—John Doll
*Assistant Examiner*—Wayne A. Langel
*Attorney, Agent, or Firm*—Birch, Stewart, Kolasch & Birch

[57] ABSTRACT

A heteropoly-acid of the formula:

$$H_{3+x}(PMo_{12-x}V_xO_{40}) \cdot nH_2O$$

wherein x and n are numbers satisfying respectively the equations: $0 \leq x \leq 3$ and $n \leq 6$, and comprising phosphorus as the central atom and molybdenum or molybdenum and vanadium as the coordinating atoms, or its reduction-form product, which is in a cubic crystal structure having diffraction lines at lattice spacings (d) of at least 8.4, 6.8, 5.9, 4.8, 4.2 and 3.4 in the X-ray powder diffraction. The heteropoly-acid is useful as a catalyst, especially as a catalyst in the production of methacrylic acid by the gas-phase catalytic oxidation of methacrolein.

9 Claims, 2 Drawing Figures

HETEROPOLY-ACIDS AND THEIR PRODUCTION AND USE

The present invention relates to heteropoly-acids, and their production and use. More particularly, it relates to novel heteropoly-acids, i.e., 12-molybdophosphoric acid and 12-molybdovanadophosphoric acid, of cubic crystal structure, and their production and use.

12-Molybdophosphoric acid and 12-molybdovanadophosphoric acid are well known to have the so-called Keggin's structure and can be separated from aqueous solutions containing oxyacid ions such as molybdate ion and phosphate ion or such as molybdate ion, metavanadate ion and phosphate ion by condensation in the presence of a mineral acid (e.g., sulfuric acid, hydrochloric acid) or a cation-exchange resin and extraction of the condensed product with ether or the like (Inorganic Chemistry, 7, 437 (1968)). A simpler method, e.g., direct synthesis from molybdenum trioxide, phosphoric acid and water or from molybdenum trioxide, vanadium pentoxide, phosphoric acid and water, is also well known.

These heteropoly-acids and their salts are solids and can take various secondary structures composed of an anion having the so-called Keggin's structure, $(PMo_{12-x}V_xO_{40})^{(3+x)-}$ $(0 \leq x \leq 3)$, and a cation. The free acids, produced as described above, generally take a diamond-like lattice (space group, Fd3m) when the largest number of crystal is contained (e.g., $H_3PMo_{12}O_{40} \cdot 30H_2O$) (Acta Cryst., B32, 1545 (1976)). Somewhat dehydrated products (e.g., $H_3PMo_{12}O_{40} \cdot 14H_2O$) are triclinic (P1−) (Z. Kristallographie, 143, 1 (1976)). Further dehydration at higher temperatures affords two or three different crystal structures. Various salts of 12-molybdophosphoric acid are known to take Fd3m and P1−, while some salts including ammonium salt take a pseudobody-centered cubic lattice (Pn3m). The structures of heteropoly-acids having the Keggin's structure is summarized in Perspect. Struct. Chem. 4, 1 (1971).

As understood from the above, the crystal structures of heteropoly-acids and their salts have been studied very well, but 12-molybdophosphoric acid and 12-molybdovanadophosphoric acid having a cubic crystal structure (space group, Pn3m) are not known.

The present invention provides heteropoly-acids, i.e., 12-molybdophosphoric acid and 12-molybdovanadophosphoric acid, representable by the formula:

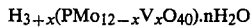

$$H_{3+x}(PMo_{12-x}V_xO_{40}) \cdot nH_2O$$

wherein x and n are numbers satisfying respectively the equations, $0 \leq x \leq 3$ and $n \leq 6$, and containing phosphorus as a central atom and molybdenum or molybdenum and vanadium as coordinating atoms, and their reduction-form products, which are in a cubic crystal structure having diffraction lines at lattice spacings (d) of at least 8.4, 6.8, 5.9, 4.8, 4.2 and 3.4 in the X-ray powder diffraction.

These compounds are obtainable by calcining the corresponding ammonium salts at a temperature of not lower than 400° C. in an inert gas and understood to be in the state of free acid from the following facts: (a) ammonium ion is scarcely detected from them in the analysis of ammoniac nitrogen; (b) the absorption due to ammonium ion at 1400 cm$^{-1}$ in the infrared absorption spectrum disappears; (c) they are easily soluble in water.

On calcination of the ammonium salts in the stream of an inert gas such as nitrogen, ammonia may be volatilized, leaving a proton. Since the produced heteropoly-acids show the so-called reduction color, i.e., bluish black, at least a part of the volatilized ammonia seems to act as a reducing agent; the heteropoly-acids are thus reduced. From the infrared absorption spectrum, it is seen that, among the characteristic absorptions at 1065 cm$^{-1}$, 965 cm$^{-1}$, 865 cm$^{-1}$ and 790 cm$^{-1}$ based on the Keggin's structure, those at 1065 cm$^{-1}$ and 865 cm$^{-1}$ are markedly decreased. In the observation of the change in the infrared absorption spectrum on reduction of $Ag_3PMo_{12}O_{40}$ with hydrogen, H. Tsuneki reports that the absorptions at 1062 cm$^{-1}$ and 863 cm$^{-1}$ decrease with the progress of the reduction [Chem. Lett., 645 (1978)]. From this, the infrared absorption spectrum of the heteropoly-acids of the invention appears to indicate that they are reduced heteropoly-acids. However, the heteropoly-acids of the invention are not limited to those in such reduction-form. On calcination at a temperature of not more than 400° C. in air, the reduction-form heteropoly-acids are re-oxidized, revealing the absorptions at 1065 cm$^{-1}$ and 865 cm$^{-1}$ in the infrared absorption spectrum. In this case, the X-ray powder diffraction pattern does not produce any material change. Thus, the original cubic system is as such retained.

In the X-ray powder diffraction, the crystal structure of the heteropoly-acids of the invention is very similar to that of the ammonium salts used as the starting materials, thus those belonging to the same simple cubic system. However, the lattice constant of the heteropolyacids shifts slightly to the larger side than with that of the ammonium salt, and, further the intensities of some peaks are somewhat different between them.

The 12-molybdophosphoric acid or 12-molybdovanadophosphoric acid of the invention can easily be produced by calcining the corresponding ammonium salt at a temperature of not lower than 400° C. in the stream of an inert gas. When the calcination of the ammonium salt is effected in air, the Keggin's structure in the heteropoly-acid gradually decomposes so as to give the crystal structure of molybdenum trioxide. In order to obtain the heteropoly-acid of cubic crystal structure, it is therefore necessary to effect the calcination in the atmosphere wherein oxygen is not materially present. The inert gas may be, for example, nitrogen, argon, carbon dioxide gas or combustion exhaust gases comprising carbon dioxide gas and steam. For calcination, temperatures of not lower than 400° C. are necessary. Since the Keggin's structure is not broken even at such a high temperature as about 600° C., temperatures up to at least 600° C. may be adopted for calcination. At temperatures below 400° C., volatilization of ammonia occurs only very slowly, making it practically difficult to convert into the free acids. The calcination time is optional, but the lower the calcination temperature, the longer time is necessary. For completion of the conversion of the ammonium salts into the free acids not containing any material amount of ammonium ion, at least about 20 hours are necessary when calcination is effected at 400° C. At a temperature of 480° C. or higher, calcination of not more than 2 hours is sufficient.

Conventional heteropoly-acids are known to be useful as catalysts for production of methacrylic acid by gas-phase catalytic oxidation of methacrolein with molecular oxygen. The heteropoly-acids of the invention are also useful as catalysts for such oxidation and exert a superior catalytic activity to conventional heteropolyacids as disclosed in Japanese Patent Publication No. 14089/1979 and their ammonium salts as disclosed in Japanese Patent Publication No. 23013/1975.

The present invention will be illustrated in more detail with reference to the following examples wherein conversion of methacrolien, yield of methacrylic acid and selectivity of methacrylic acid are defined as follows:

$$\text{Conversion of methacrolein (\%)} = \frac{\text{Number of moles of methacrolein reacted}}{\text{Number of moles of methacrolein supplied}} \times 100$$

$$\text{Yield of methacrylic acid (\%)} = \frac{\text{Number of moles of methacrylic acid produced}}{\text{Number of moles of methacrolein supplied}} \times 100$$

$$\text{Selectivity of methacrylic acid (\%)} = \frac{\text{Yield of methacrylic acid}}{\text{Conversion of methacrolein}} \times 100$$

EXAMPLE 1

Figure 1:
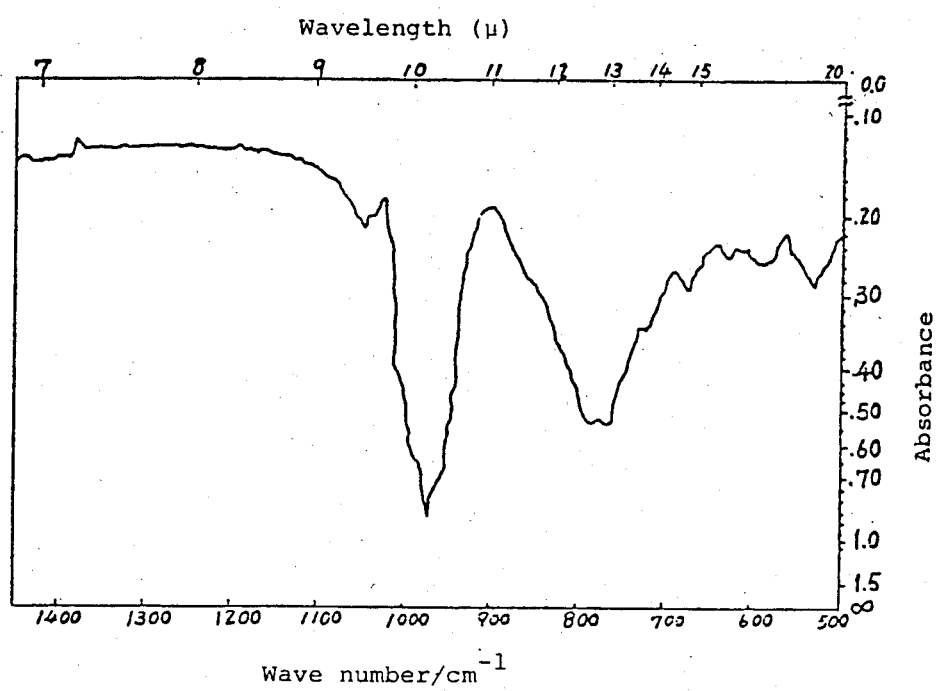
FIG. 1 shows the infrared absorption spectrum determined by the KBr tablet method of 12-molybdophosphoric acid obtained according to the present invention.

Commercially available ammonium 12-molybdophosphate $((NH_4)_3PMo_{12}O_{40} \cdot nH_2O)$ was calcined at 520° C. for 2 hours in nitrogen atmosphere to obtain 12-molybdophosphoric acid. The powder 12-molybdophosphoric acid thus obtained was blackish blue and readily soluble in water. The X-ray powder diffraction is as shown in Table 1, and the infrared absorption spectrum determined by the KBr tablet method is as shown in FIG. 1.

TABLE 1

| 12-Molybdophosphoric acid (Simple cubic system; $a_0 = 11.86$ Å; $Z = 4$) | | | | |
|---|---|---|---|---|
| d (Å) | $I/I_1$ | h | k | l |
| 8.4 | 62 | 1 | 1 | 0 |
| 6.85 | 2 | 1 | 1 | 1 |
| 5.93 | 7 | 2 | 0 | 0 |
| 4.84 | 39 | 2 | 1 | 1 |
| 4.19 | 30 | 2 | 2 | 0 |
| 3.95 | 0 | 2 | 2 | 1 |
| 3.75 | 1 | 3 | 1 | 0 |
| 3.58 | 0 | 3 | 1 | 1 |
| 3.42 | 100 | 2 | 2 | 2 |
| 3.17 | 6 | 3 | 2 | 1 |

COMPARATIVE EXAMPLES 1 AND 2

Ammonium 12-molybdophosphate $((NH_4)_3PMo_{12}O_{40} \cdot nH_2O)$ and 12-molybdophosphoric acids $(H_3PMo_{12}O_{40} \cdot 29 \sim 30H_2O$ and $H_3PMo_{12}O_{40} \cdot 14H_2O)$, all of which were commercially available, were dried over silica gel in a desiccator overnight. The X-ray powder diffractions of the products are shown in Tables 2, 3 and 4.

TABLE 2

| Ammonium 12-molybdophosphate (Simple cubic system; $a_0 = 11.67$ Å; Pn3m, $Z = 4$) | | | | |
|---|---|---|---|---|
| d (Å) | $I/I_0$ | h | k | l |
| 8.25 | 67 | 1 | 1 | 0 |
| 6.74 | 3 | 1 | 1 | 1 |
| 5.84 | 22 | 2 | 0 | 0 |
| 4.76 | 9 | 2 | 1 | 1 |
| 4.13 | 28 | 2 | 2 | 0 |
| 3.89 | 0 | 2 | 2 | 1 |
| 3.69 | 8 | 3 | 1 | 0 |
| 3.52 | 0 | 3 | 1 | 1 |
| 3.37 | 100 | 2 | 2 | 2 |
| 3.12 | 4 | 3 | 2 | 1 |

TABLE 3

| $H_3PMo_{12}O_{40} \cdot 30H_2O$ (Face-centered cubic system; $a_0 = 23.25$ Å; Fd3m, $Z = 8$) | | | | |
|---|---|---|---|---|
| d (Å) | $I/I_1$ | h | k | l |
| 13.4 | 100 | 1 | 1 | 1 |
| 8.2 | 20 | 2 | 2 | 0 |
| 7.0 | 1 | 3 | 1 | 1 |
| 5.8 | 5 | 4 | 0 | 0 |
| 5.33 | 7 | 3 | 3 | 1 |
| 4.75 | 2 | 4 | 2 | 2 |
| 4.48 | 10 | 5 | 1 | 1 |
| | | 3 | 3 | 3 |
| 4.11 | 7 | 4 | 4 | 0 |
| 3.93 | 4 | 5 | 3 | 1 |
| 3.67 | 2 | 6 | 2 | 0 |
| 3.55 | 8 | 5 | 3 | 3 |
| 3.36 | 27 | 4 | 4 | 4 |
| 3.26 | 5 | 7 | 1 | 1 |
| | | 5 | 5 | 1 |
| 3.11 | 1 | 6 | 4 | 2 |
| 3.03 | 9 | 5 | 5 | 3 |
| | | 7 | 3 | 1 |

TABLE 4

| $H_3PMo_{12}O_{40} \cdot 14H_2O$ (Triclinic system; $a = 14.10$ Å, $b = 14.13$ Å, $c = 13.55$ Å, $\alpha = 112.1$, $\beta = 109.8$, $\gamma = 60.7$, $P_1-$, $Z = 2$) | | | | |
|---|---|---|---|---|
| d (Å) | $I/I_1$ | h | k | l |
| 12.3 | 30 | 0 | 0 | 1 |
| 11.1 | 100 | 1 | 1 | 0 |
| 9.9 | 90 | 0 | 1 | 1 |
| 9.6 | 60 | 1 | 0 | 1 |
| 7.9 | 8 | 1 | 0 | 1 |
| 7.6 | 5 | 0 | 1 | 1 |
| 5.5 | 8 | 2 | 2 | 0 |
| 5.1 | 10 | — | | |
| 5.0 | 25 | — | | |
| 4.8 | 40 | — | | |
| . | . | | | |
| . | . | | | |
| 3.40 | 60 | — | | |
| 3.21 | 95 | — | | |
| 3.16 | 50 | — | | |
| 3.10 | 85 | — | | |

Figure 2:
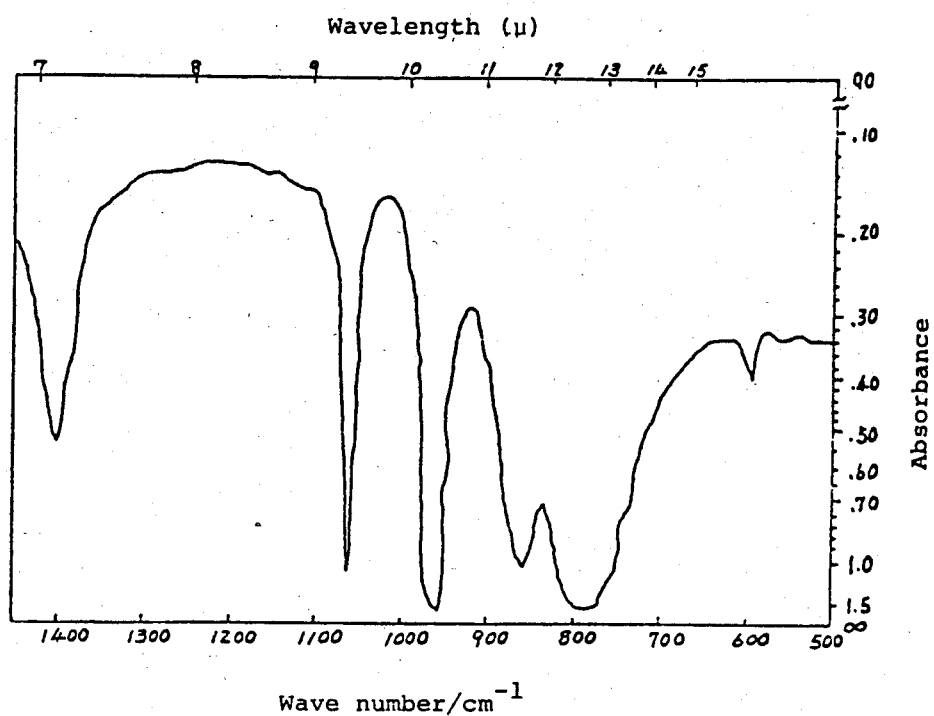
FIG. 2 shows the infrared absorption spectrum of commercially available ammonium 12-molybdophosphate.

The X-ray powder diffraction in Table 1 is very similar to that in Table 2 (ammonium salt), and those can be indexed as the same simple cubic system. It is completely different from the results (Tables 3 and 4) obtained with conventional free acids. On comparison of the infrared absorption spectra, it can be seen that, with the novel heteropoly-acid (FIG. 1), the absorption of ammonium ion at 1400 cm$^{-1}$ as observed in FIG. 2 disappeared. Further, the absorptions at 1065 cm$^{-1}$ and 865 cm$^{-1}$ present in FIG. 2 and characteristic to heteropoly-acids became very small in FIG. 1.

EXAMPLE 2

121 Grams of sodium molybdate (Na$_2$MoO$_4$.2H$_2$O) were dissolved in 200 ml of water. Separately, a solution of 17.9 g of disodium hydrogen phosphate (Na$_2$HPO$_4$.12H$_2$O) in 100 ml of water and a solution prepared by dissolving 24.4 g of sodium metavanadate (NaVO$_3$) in 100 ml of water by heating were mixed together and cooled, and 5 ml of conc. sulfuric acid were added thereto. The solution thus obtained was added to the previously prepared sodium molybdate solution, and 85 ml of conc. sulfuric acid were gradually added thereto with vigorous stirring. Thereafter, this solution was cooled, and after adding 500 ml of ethyl ether thereto, it was placed in a separating funnel, shaken and then allowed to stand. The red middle layer was taken out and air-dried to obtain 10-molybdo-2-vanadophosphoric acid (H$_5$PMo$_{10}$V$_2$O$_{40}$.nH$_2$O) as crystals. The X-ray diffraction of this product was almost the same as in Table 3. This 10-molybdo-2-vanadophosphoric acid was dissolved in 100 ml of water, and a solution of 5.2 g of ammonium nitrate (NH$_4$NO$_3$) in 100 ml of water was added thereto, whereby an orange precipitate was formed. This precipitate was separated by centrifugation and dried to obtain ammonium 10-molybdo-2-vanadophosphate ((NH$_4$)$_3$H$_2$PMo$_{10}$V$_2$O$_{40}$.nH$_2$O). The X-ray diffraction of this product was almost the same as in Table 2. The ammonium 10-molybdo-2-vanadophosphate was then calcined at 480° C. for 2 hours in nitrogen atmosphere to obtain a blackish blue powder. This product gave almost the same X-ray diffraction pattern as in Table 1. The ammoniac nitrogen contents of the ammonium 10-molybdo-2-vanadophosphate and of the blackish blue powder were 2.52% by weight and 0.00% by weight, respectively.

EXAMPLE 3

Using as the catalyst 10-molybdo-2-vanadophosphoric acid (3-0) as prepared in Example 2, or conventional 10-molybdo-2-vanadophosphoric acid (3-1) or its ammonium salt (3-2), methacrylic acid was produced by gas-phase catalytic oxidation of methacrolein. Namely, the material for the catalyst was shaped into tablets and pulverized to obtain particles of 24 to 32 mesh size. The particles (10 ml) were packed in a glass tubular reactor of 12 mm in inner diameter. A feed gas comprising 3.7 mole % of methacrolein, 7.4 mole % of oxygen, 74 mole % of nitrogen and 14.9 mole % of steam was passed through the reactor with a space velocity (SV) of 1800 hr$^{-1}$ (NTP standard), and the catalytic activity test was carried out at a reaction temperature of 320° C. The results are shown in Table 5, from which it is understood that the heteropoly-acid of the invention gives a larger conversion of methacrolein.

EXAMPLE 4

13.8 Grams of 85% by weight phosphoric acid were added to 2 liters of deionized water, followed by stirring. Thereafter, 212 g of ammonium molybdate ((NH$_4$)$_6$Mo$_7$O$_{24}$.4H$_2$O) were gradually added thereto. To the resulting solution, a solution of 11.7 g of ammonium metavanadate (NH$_4$VO$_3$) in 100 ml of hot water and a solution of 12.1 g of copper nitrate (Cu(NO$_3$)$_2$.3H$_2$O) in 50 ml of water were added, and the mixed solution obtained was heated and evaporated to dryness. The residue was calcined at 230° C. for 4 hours, pulverized and shaped into tablets of 5 mm in diameter and 5 mm thick. The tablets were divided into halves, and one half was calcined at 450° C. for 4 hours in nitrogen stream to obtain a catalyst (4-0). The other half was calcined at 380° C. for 4 hours in air to give another catalyst (4-1). The X-ray diffraction showed that the catalysts (4-0) and (4-1) are nearly the same as in Tables 1 and 2, respectively. The ammoniac nitrogen contents of the catalysts (4-0) and (4-1) were 0.01% by weight and 2.48% by weight, respectively. The compositions of both catalysts, exclusive of oxygen, hydrogen and nitrogen, corresponded to P$_{1.2}$Mo$_{12}$V$_1$Cu$_{0.5}$.

EXAMPLE 5

The catalysts (4-0) and (4-1) as obtained in Example 4 were pulverized, and the catalytic activity test was carried out under the same condition as in Example 3 except that the reaction temperature was 300° C. The results are shown in Table 5, from which it can be seen that the catalyst containing the heteropoly-acid of the invention gives a larger conversion of methacrolein than the catalyst not containing such heteropoly-acid. Thus, the catalyst containing the heteropoly-acid of the invention is highly active even at lower temperatures.

TABLE 5

| No. | Catalyst | Conversion of methacrolein (%) | Yield of methacrylic acid (%) | Selectivity of methacrylic acid (%) | Reaction temperature (°C.) |
|---|---|---|---|---|---|
| 3-0 | H$_5$PMo$_{10}$V$_2$O$_{40}$.nH$_2$O 480° C., 2 hrs | 69.8 | 56.7 | 81.2 | 320 |
| 3-1 | H$_5$PMo$_{10}$V$_2$O$_{40}$.30H$_2$O (dried at 120° C.) | 58.3 | 48.2 | 82.6 | 320 |
| 3-2 | (NH$_4$)$_3$H$_2$PMo$_{10}$V$_2$O$_{40}$.nH$_2$O | 36.5 | 30.8 | 84.3 | 320 |
| 4-0 | 9$_{1.2}$Mo$_{12}$V$_1$Cu$_{0.5}$ 450° C., N$_2$, 4 hrs | 86.3 | 71.9 | 83.3 | 300 |
| 4-1 | P$_{1.2}$Mo$_{12}$V$_1$Cu$_{0.5}$ 380° C., air, 4 hrs | 78.8 | 66.3 | 84.2 | 300 |

Note:
Gas composition, methacrolein:oxygen:nitrogen:steam = 3.7:7.4:74:14.9. Space velocity (SV), 1800 hr$^{-1}$. Nos. 3-0 and 4-0 are of the invention, and Nos. 3-1, 3-2 and 4-1 are for comparison.

What is claimed is:

1. A heteropoly-acid of the formula:

$$H_{3+x}(PMo_{12-x}V_xO_{40}).nH_2O$$

wherein x and n are numbers satisfying respectively the equations: $0 \leq x \leq 3$ and $n \leq 6$, and comprising phosphorus as the central atom and molybdenum or molybdenum and vanadium as the coordinating atoms, or its reduction-form product, which is in a cubic crystal structure having diffraction lines at lattice spacings (d)

of at least 8.4, 6.8, 5.9, 4.8, 4.2 and 3.4 in the X-ray powder diffraction.

2. A method for producing the heteropoly-acid according to claim 1, comprising calcining the ammonium salt of 12-molybdophosphoric acid or 12-molybdovanadophosphoric acid at a temperature of not lower than 400° C. in an inert atmosphere consisting essentially of an inert gas.

3. The method of claim 2, wherein the inert gas is selected from the group consisting of nitrogen, argon, carbon dioxide and combustion exhaust gases comprising carbon dioxide gas and steam.

4. The method of claim 2, wherein the inert gas is nitrogen.

5. A heteropoly-acid of the formula:

$$H_{3+x}(PMo_{12-x}V_xO_{40}) \cdot nH_2O$$

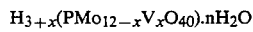

wherein x and n are numbers satisfying respectively the equations: $0 \leq x \leq 3$ and $n \leq 6$, and comprising phosphorus as the central atom and molybdenum or molybdenum and vanadium as the coordinating atoms, or its reduction-form product, which is in a cubic crystal structure having diffraction lines at lattice spacings (d) of at least 8.4, 6.8, 5.9, 4.8, 4.2 and 3.4 in the X-ray powder diffraction which is produced by a process which comprises calcining the ammonium salt of 12-molybdophosphoric acid or 12-molybdovanadophosphoric acid in an inert atmosphere consisting essentially of an inert gas.

6. The heteropoly-acid of claim 5, which has essentially the following X-ray powder diffraction (Simple cubic system; $a_0$ is 11.86 Å and Z is 4)

| d (Å) | I/I$_1$ | h | k | l |
|-------|---------|---|---|---|
| 8.4   | 62      | 1 | 1 | 0 |
| 6.85  | 2       | 1 | 1 | 1 |
| 5.93  | 7       | 2 | 0 | 0 |
| 4.84  | 39      | 2 | 1 | 1 |
| 4.19  | 30      | 2 | 2 | 0 |
| 3.95  | 0       | 2 | 2 | 1 |
| 3.75  | 1       | 3 | 1 | 0 |
| 3.58  | 0       | 3 | 1 | 1 |
| 3.42  | 100     | 2 | 2 | 2 |
| 3.17  | 6       | 3 | 2 | 1 |

7. The heteropoly-acid of claim 5, which has essentially the absorption spectrum determined by the KBr tablet method as shown in FIG. 1.

8. The heteropoly-acid of claim 5, wherein the inert gas is selected from the group consisting of nitrogen, argon, carbon dioxide and combustion exhaust gases comprising carbon dioxide and steam.

9. The heteropoly-acid of claim 5, wherein the inert gas is nitrogen.

* * * * *